United States Patent [19]

Jones

[11] Patent Number: 4,493,485
[45] Date of Patent: Jan. 15, 1985

[54] EXERCISING APPARATUS AND METHOD
[75] Inventor: Arthur A. Jones, Lake Helen, Fla.
[73] Assignee: Nautilus Sports/Medical Industries, Inc., Lake Helen, Fla.
[21] Appl. No.: 495,575
[22] Filed: Jun. 24, 1983

Related U.S. Application Data

[63] Continuation of Ser. No. 229,922, Jan. 30, 1981, abandoned.

[51] Int. Cl.³ .............................................. A63B 21/00
[52] U.S. Cl. .................................... 272/126; 272/134; 272/DIG. 5; 272/125; 73/379
[58] Field of Search .................. 272/69, 70, 72, 73, 272/93, 96, 125, 126, 134, DIG. 5

[56] References Cited

U.S. PATENT DOCUMENTS

| | | |
|---|---|---|
| 3,529,474 | 9/1970 | Olson . |
| 3,745,990 | 7/1973 | Neis . |
| 3,784,194 | 1/1974 | Perrine ............................... 272/130 |
| 3,869,121 | 3/1975 | Flavell . |
| 4,071,235 | 1/1978 | Zent ..................................... 272/73 |
| 4,244,021 | 1/1981 | Chiles .................................. 272/73 |
| 4,306,714 | 12/1981 | Loomis et al. ...................... 272/96 |

FOREIGN PATENT DOCUMENTS

925678  5/1963  United Kingdom .
1406342  9/1975  United Kingdom .

Primary Examiner—Richard C. Pinkham
Assistant Examiner—Leo P. Picard
Attorney, Agent, or Firm—Bell, Seltzer, Park & Gibson

[57] ABSTRACT

An exercising apparatus and method incorporating an open loop system which monitors the activity of an exercising person and directs such activity by displaying the correlation of such activity with a programmed regimen. The apparatus is engaged by body portions of the exercising person operating the apparatus and preferably guides the person in "full range" exercise while monitoring and displaying a representation of work performed during exercising movement. Specific arrangements for using force exerted by one body portion to provide resistance to be overcome by another body portion are shown and described, as is an arrangement for monitoring the use of a number of apparatus so as to monitor a full physiological development program.

18 Claims, 12 Drawing Figures

EXERCISING APPARATUS AND METHOD

This application is a continuation of application Ser. No. 229,922 filed Jan. 30, 1981 now abandoned.

FIELD AND BACKGROUND OF INVENTION

Planned programs of exercise have long been followed by persons training for athletic events of various types or pursuing a course of treatment for the rehabilitation of an illness, injury or the like. Many such planned programs of exercise have employed aids which have, in recent years, come to take the form of various apparatus or machines which facilitate the planned programs of exercise. Such apparatus, machines and methods have grown out of various concepts and studies regarding physiology and physiological development and function.

One type of apparatus and method which has been used with significant success is full range exercise such as is possible, for example, through use of the apparatus of Jones, U.S. Pat. No. 3,858,873. "Full range" exercise as used with reference to such an apparatus and method, and as used in the description which follows, is a defined term. The defined term "full range exercise" refers to exercise having positive work; negative work; rotary form movement; stretching; prestretching; automatically variable, balanced, direct resistance; resistance in the position of full muscular contraction; and unrestricted speed of movement. The interested reader is referred to available publications for further explication of these characteristic features of full range exercise.

It is recognized, however, that not all exercise need be full range exercise as here defined. More specifically, certain exercise movements are compound movements which cannot attain the characteristics of full range exercise as listed briefly above due to the presence of "lock out" positions and non-rotary movements. Such exercise may, for example, be realized through the use of apparatus such as that disclosed in Mazman U.S. Pat. No. 3,905,599.

The general field of such exercise and related apparatus and methods is here referred to as "exercise physiology". The field of exercise physiology is related to sports medicine, being the field of medical study which is particularly directed to athletic sports and the like. While it has become possible, within these fields, to develop exercise programs which apply methods and apparatus of the types briefly mentioned above with greater specificity than has been possible heretofore, exercise physiology and related areas of sports medicine have continued to be inherently imprecise. A major difficulty in accomplishing precise application of exercising programs has been in the difficulty of monitoring, directing and recording physiological performance.

BRIEF DESCRIPTION OF INVENTION

It is an object of the present invention to improve the accuracy and precision by which physiological performance is monitored, directed and recorded. In realizing this object of the present invention, exercise apparatus having means engaged by a body portion of an exercising person operating the apparatus is improved by the provision of an open loop system for monitoring the physical effort exerted by the exercising person and for correlating the monitored effort exerted to a programmed standard. The open loop system displays a representation of the correlation of the monitored effort exerted to the programmed standard, in such a manner as to direct the physiological performance of the exercising program.

Yet a further object of the present invention is to provide, in an exercising apparatus of the type described and which has means for imposing resistance to musculature effecting movement of a body portion of an exercising person and for causing the musculature to perform positive and negative work during movement, means for responding to the exertion of force and for signaling the magnitude of the force exerted and the position of movement from which such force is exerted. Additionally, a monitoring and display means operatively connected with the apparatus receives signals and displays for an exercising person operating the apparatus a representation of the work performed during movement of an exercised portion of the body.

Yet a further object of the present invention is to accomplish, during exercise, an accurate and precise recording of the conditions of the exercise in terms of force exerted, body position from which force is exerted, speed of movement during exertion of force, and range of movement over which force is exerted. By recording such information during exercising, physiological performance may, for the first time, be systematically analyzed and developed to achieve desirable efficiencies and performance.

BRIEF DESCRIPTION OF DRAWINGS

Some of the objects of the invention having been stated, other objects will appear as the description proceeds, when taken in connection with the accompanying drawings, in which—

DETAILED DESCRIPTION OF INVENTION

While the present invention will be described hereinafter with particular reference to the accompanying drawings, in which certain operating embodiments of the apparatus of the present invention are shown, it is to be understood at the outset of the description which follows that it is contemplated that apparatus and methods in accordance with the present invention may be varied from the specific forms described hereinafter, while still attaining the desired result of this invention. Accordingly, the description which follows is to be understood as a broad teaching disclosure directed to persons of appropriate skill in the appropriate arts, and not as limiting upon the scope of this invention.

Figure 1:
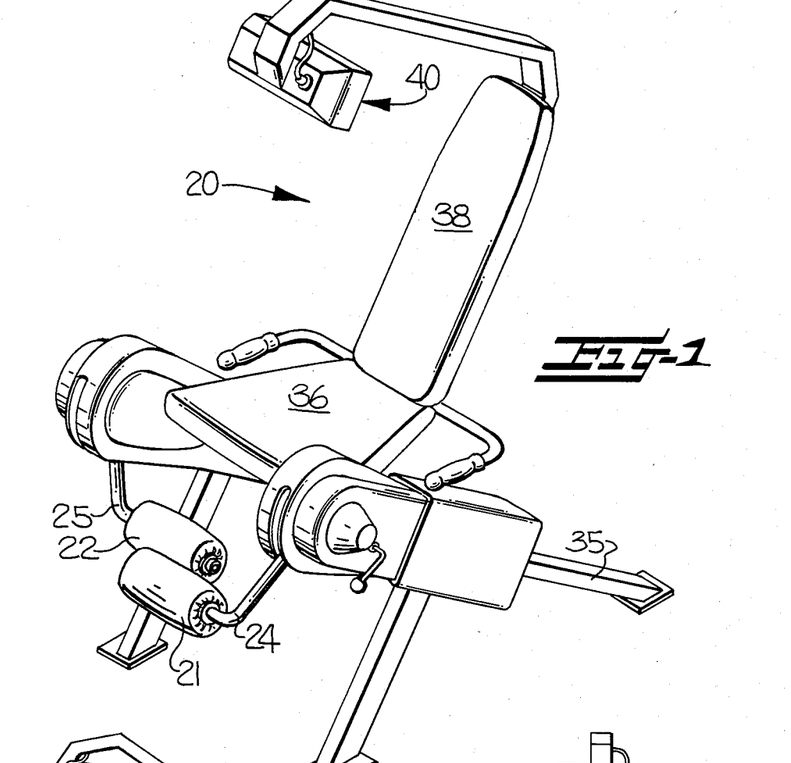
FIG. 1 is a perspective view of a leg extension exercise apparatus embodying the present invention.
Figure 2:
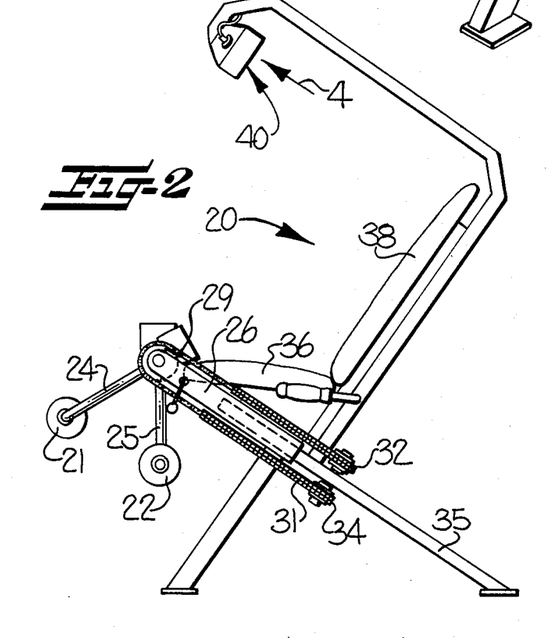
FIG. 2 is a side elevation view of the exercise apparatus of FIG. 1, with certain cover components removed in order to make certain operating elements of the apparatus more readily visible.
Figure 3:
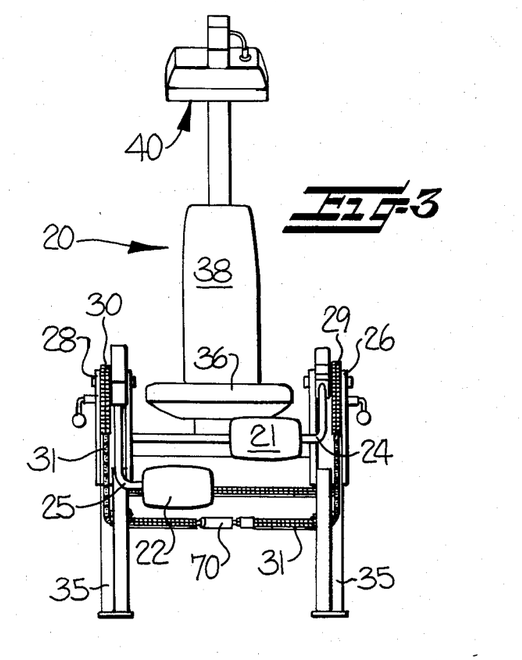
FIG. 3 is a front elevation view of the apparatus of FIG. 2.

Referring now to FIGS. 1 through 3, an exercise apparatus embodying the present invention is there illustrated in the form of a leg extension apparatus generally indicated at 20. In the form illustrated, the apparatus 20 is a full range exercise apparatus having means engaged by body portions of an exercising person operating the apparatus. By means of mounting arrangements provided and operative coupling of elements with the body engaging means, the body engaging means rotates about an axis substantially coaxial with the axis of rotation of an engaged body portion of an exercising person and imposes throughout a full range of movement of the engaged body portion an automatically variable, balanced, direct resistance to the musculature effecting movement thereof. The imposition of resistance occurs while an unrestricted speed of movement is accommodated and so as to cause the musculature of the exercising person to perform both positive and negative work, and to be subjected to stretching and prestretching, all during rotary form movement of the engaged body portion. In the specific form illustrated, the leg extension apparatus 20 has first and second roll members 21, 22 respectively engaged by shin surfaces of the left and right legs of an exercising person operating the apparatus 20. Each of the first and second roll members 21, 22 is mounted for rotation about an axis, by means of arm members 24, 25. In use, the axes of rotation of the arm members 24, 25 and roll members 21, 22 moving therewith are substantially coaxial with the axis of rotation at the knees of the person operating the apparatus 20.

In the form of apparatus illustrated in FIGS. 1 through 3, means are provided which are operatively coupled with the first and second body engaging means 21, 22 for imposing throughout a full range of movement of the lower leg portions of the exercising person a resistance of the type described. In particular, each of the arm members 24, 25 is joined, near the axis of rotation thereof, with a stub shaft which extends through a side frame structure of the apparatus 20. The side frame structures include side frame members 26, 28. Affixed to the respective shafts are sprockets 29, 30 about which is trained a chain 31. The chain 31 is formed as an essentially closed loop, passes over rear sprockets such as the sprockets 32, 34 mounted on a rear leg member 35, and are arranged so that upward movement of one roll member 21 brings about downward movement of the other roll member 22, and vice versa. As will be understood, the positive work being done by one lower leg (for example, the left lower leg of an exercising person) provides, through the chain 31, the resistance which brings about negative work done by the other body portion (for example, the right leg). Thus, in the form of apparatus 20 illustrated in FIGS. 1 through 3, all resistance provided is provided by the exercising person. Further, the rate of work is governed by the exercising person. The apparatus 20 thus is both quite safe, in that no force is generated by the apparatus 20 itself, and requires the user to develop coordination skills in that the exercising person must consciously produce the required force and speed in exercising. These features relate to other characteristics of the present invention as described more fully hereinafter.

In using the apparatus of FIGS. 1 through 3, an exercising person assumes a position seated upon a seat portion 36, which is mounted on the frame of the apparatus 20, and leans backward against a backrest portion 38. The users legs, dangling forwardly over the front edge of the seat 36, are positioned for substantially coaxial alignment of the knee joint and the rotational axes for the roll members 21, 22. As so positioned, the user is supported so as to be able to readily view a display generally indicated at 40 and described more fully hereinafter.

In accordance with important features of this invention, open loop means are operatively coupled with the body engaging means of the apparatus 20 for monitoring physical effort exerted by an exercising person operating the apparatus and for correlating monitored effort exerted to a programmed standard and for displaying, by means of the display generally indicated at 40, a representation of the correlation of monitored effort exerted to the programmed standard. It is significant to the present subject invention that the apparatus 20 includes an open loop means. As is familiar to persons skilled in the art of servomechanisms, a closed loop involves feeding back into an apparatus some signal derived from the action of the apparatus. In the specific instance of an exercise apparatus, such as "closed loop" might involve a servo-mechanism for exerting force with respect to an exercising person. Such servomechanisms have an inherent risk of injury, in that the servomechanism may become unstable or may fail in such a way as to inflict serious injury to the exercising person. That is not the case in the apparatus 20 of the present invention. In the apparatus 20 of the present invention, closure of the open loop, if any, occurs through the actions of the exercising person who, as briefly indicated above, maintains control over the force exerted, the speed of movement, and the consequent work done and physical effort exerted. In the form shown, this remains particularly true inasmuch as the sole source of force exerted is the exercising person. However, it is known that essentially the same characteristics follow where a weight stack or the like is used as a portion or all of the force exerting means. Use of a weight stack or the like simply presents an additional preset or predetermined factor to be taken into account in operation of the apparatus as described more fully hereinafter.

In the form contemplated for the apparatus 20 of FIGS. 1 through 3, the open loop system includes means operatively coupled with the roll members 21, 22 for responding to exertion of force between those body engaging means and the engaged shin portions and for signalling the magnitude of force exerted. Preferably, the force responsive and signalling means comprises a load cell inserted into the chain 31 as a link thereof and which develops an appropriate analogue electrical signal. One form of load cell which has been employed successfully in apparatus such as the apparatus 20 of FIGS. 1 through 3 is an electrical resistance strain gauge which varies in resistance as force is exerted thereon. Means are additionally operatively coupled with the body engaging roll members 21, 22 for responding to movement thereof and for signalling the position thereof. Preferably, the position responsive signalling means takes the form of a pair of potentiometers aligned with the shafts which carry the upper front sprockets 29, 30 and which define the axis of rotation for the roll members 21, 22. Potentiometers, used at this point, signal the position of the arms 24, 25 and the roll members 21, 22 by variations in resistance value.

While it is recognized that the chaining together of the arms 24, 25 as described hereinabove, by means of the chain 31 which includes the load cell, essentially coordinates the movement of the two arms and the body engaging means carried thereby, opening the possibility of using a single position signalling means, it is preferred to provide two position signalling means as described above. The use of two signalling means reduces the possibility of introducing error due to chain stretch and the like.

Figure 4:
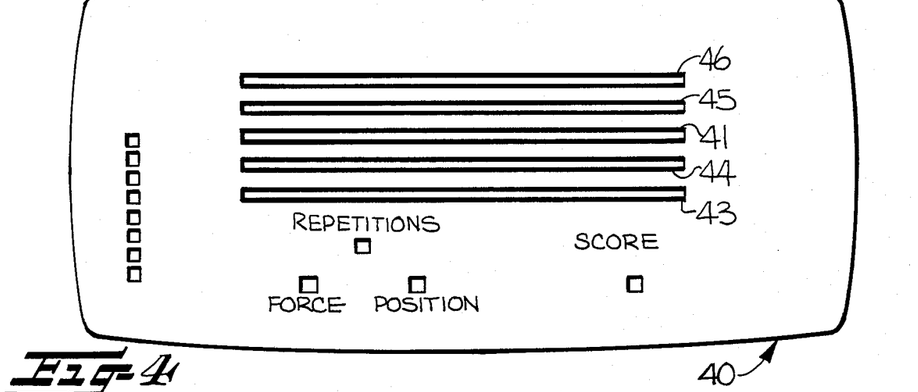
FIG. 4 is a view of a display incorporated in the apparatus of FIGS. 1 through 3, taken generally as indicated by the arrow 4 in FIG. 2.

The load cell and the position signalling potentiometers are operatively connected with and supply signals to a monitoring and display means which includes the display visible to a user of the apparatus 20 in the housing 40 as briefly described above. The display, as visible to the user of the apparatus 20, is illustrated in FIG. 4 and includes both analogue and digital information. The display means is operated under the control of digital processing means operatively connected with the analogue signalling means described hereinabove. The digital processing means preferably includes a microcomputer or processor forming an integral part of the apparatus 20. The digital processing means includes a stored program means for retaining instructions regarding at least one of a standard magnitude of force to be exerted by an exercising person and a standard rate of exertion of force by the exercising person and a standard number of repetitions of cyclical force exertion.

Use of a microprocessor or microcomputer as a component of the apparatus 20, as described hereinabove, provides a range of significant advantages for the apparatus of the present invention, particularly in an environment such as a laboratory, health club or spa in which a plurality of machines of various types may be present. The apparatus 20, with a microprocessor or microcomputer as a component thereof, is an "intelligent machine". That is, the machine can identify a particular user from a code entered manually or by means of a coded card or the like and can communicate with a central processing unit which monitors a plurality of apparatus for retrieving from a memory which forms a portion of the apparatus 20 or which forms a portion of the central processing unit a particular exercise regimen to be followed by a particular user. Further, as the exercise regimen is carried out, the force applied by the exercising person and the position from which force is applied are monitored continuously and the information derived from the monitoring is processed. As a consequence, the user while operating the apparatus 20 may view a display of the representation of the user's signalled effort and its correlation to the user's programmed regimen of exercise.

In the particular form of the display illustrated in FIG. 4, a plurality of generally horizontal indicator lines are provided, respectively identified in FIG. 4 at 41, and 43 through 46. Line 41 is used to display a progressive pacing signal which may, for examle, take the form of a gradually extending lighted line moving from one side of the display toward the other at a timed rate. Such a display may be generated for example, by successively signalling a series of light emitting diodes. The other display lines 43 through 46 may have similar devices which may be successively signalled to provide an analogue display of a gradually extending lighted line. The display to be generated on the other display lines 43 through 46 is responsive to exercise effort exerted by the exercising person and thus will move from one side of the display toward the other at a rate dependent upon the rate of movement of the exercising person. Further, the signal will move from one to another of the lines 43 through 46 in response to variations in force exerted. That is, an exercising movement performed at an indicated rate but with low levels of force will be displayed only on line 43. An exercising effort which involved exertion of varying levels of force might begin a trace on the lowermost line 43, move upward through lines 44 and 45 to line 46, and then return back toward the lowermost line 43. As pointed out more fully hereinafter, a predetermined profile for the effort to be exerted by the exercising person and the pacing of that effort may be coordinated with signalled force and position so that, when the programmed regimen is followed, the user responsive trace or gradually extending line tracks constantly along a single predetermined line such as the line 44 in coordination with the pace of the progressive pacing signal extending along the line 41. With an apparatus such as the leg extension apparatus 20 described above, indicator signals to either side of the display area occupied by the lines 41 and 43 through 46 may be used to indicate which limb or body portion is to be engaged in doing positive work at any given moment.

Figure 5:
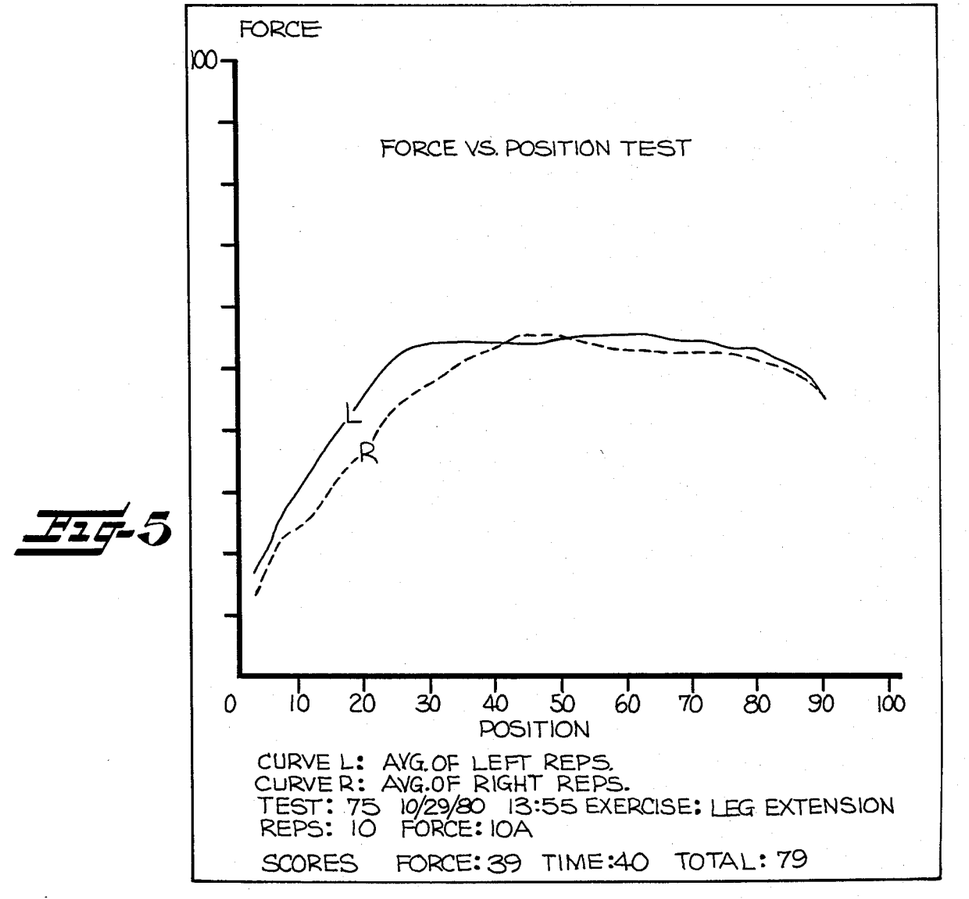
FIG. 5 is a graphic representation of one form of data display available from the apparatus of FIGS. 1 through 3, in accordance with the present invention.

An exercise regimen designed for use with an apparatus such as the leg extension machine 20 typically will involve a predetermined number of repetitions of cycles of movement. As repetitions occur, a digital display presents numerical indicia of the number of repetitions which have been completed. At the conclusion of the number of repetitions programmed by the regimen, then the average force exerted and the average interval of time required for a repetition may be displayed as numerical indicia and combined into a score.

Where a plotting attachment or a printer is associated with the central processing unit, the information thus derived may also be presented in graphic form. One form of graphic representation is illustrated in FIG. 5, where curves have been plotted as the average of repetitions by the left leg and repetitions by the right leg for an exercising person using a leg extension machine.

The present invention contemplates that operation of exercise machines in accordance with a stored program may involve operation of the apparatus with the microprocessor unit (MPU) which forms a portion of an individual apparatus or by cooperation between the MPU and a central processor unit (CPU). In instances where operation is essentially under the control of an MPU, instructions regarding the standard magnitude of force to be exerted by the exercising person and the standard rate of exertion of force by the exercising person and the standard number of repetitions of cyclical force exertion will be entered directly at the MPU, either manually by the exercising person prior to beginning use of the apparatus 20 or from a stored record card such as a punched card or a magnetic record bearing card which may be inserted into a reader at the apparatus 20. Where operation is in coordination with a CPU, the greater information storage capabilities of the CPU may permit operation in accordance with a procedure wherein an individual merely identifies themselves to the CPU and the CPU thereupon loads into the MPU the instructions required.

Figure 6:
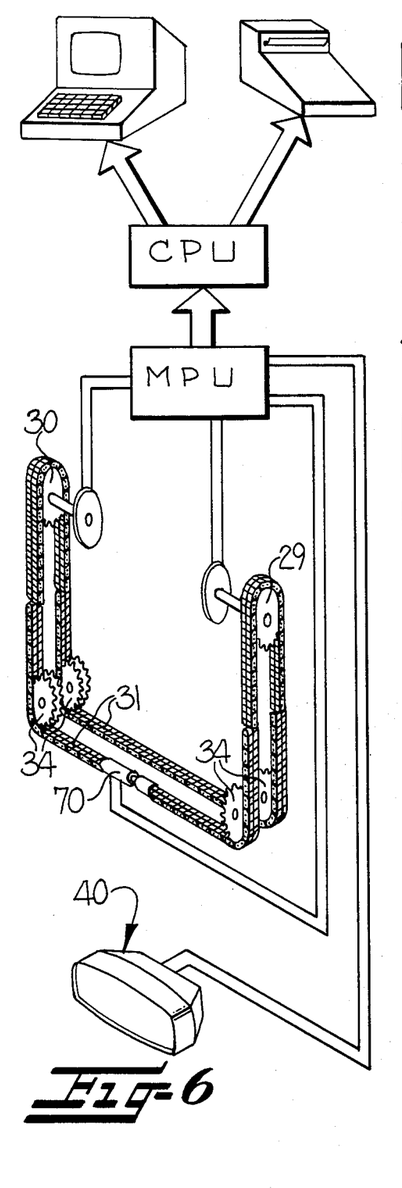
FIG. 6 is a schematic representation of the interconnection of and communication among certain apparatus used in accordance with the methods of this invention.

The components involved in operation as described hereinabove may be as schematically represented in FIG. 6, where the analogue signalling devices incorporated into an exercising apparatus are indicated, as are the MPU, display and CPU.

In circumstances where a CPU is used in association with exercise machines, the "intelligent machine" characteristic of exercise apparatus in accordance with the present invention permits a single CPU to be shared among and communicate with a plurality of individual exercise machines. This is significant in that up to at least thirty-two (32) distinct types of exercise machines are contemplated as being useful along the general lines described hereinabove with specific reference to the leg extension machine 20. Thus, a single CPU may monitor, process and display information derived from a plurality of exercise apparatus. The CPU may also direct the full exercise regimen of an individual using the facility so equipped.

Figure 7:
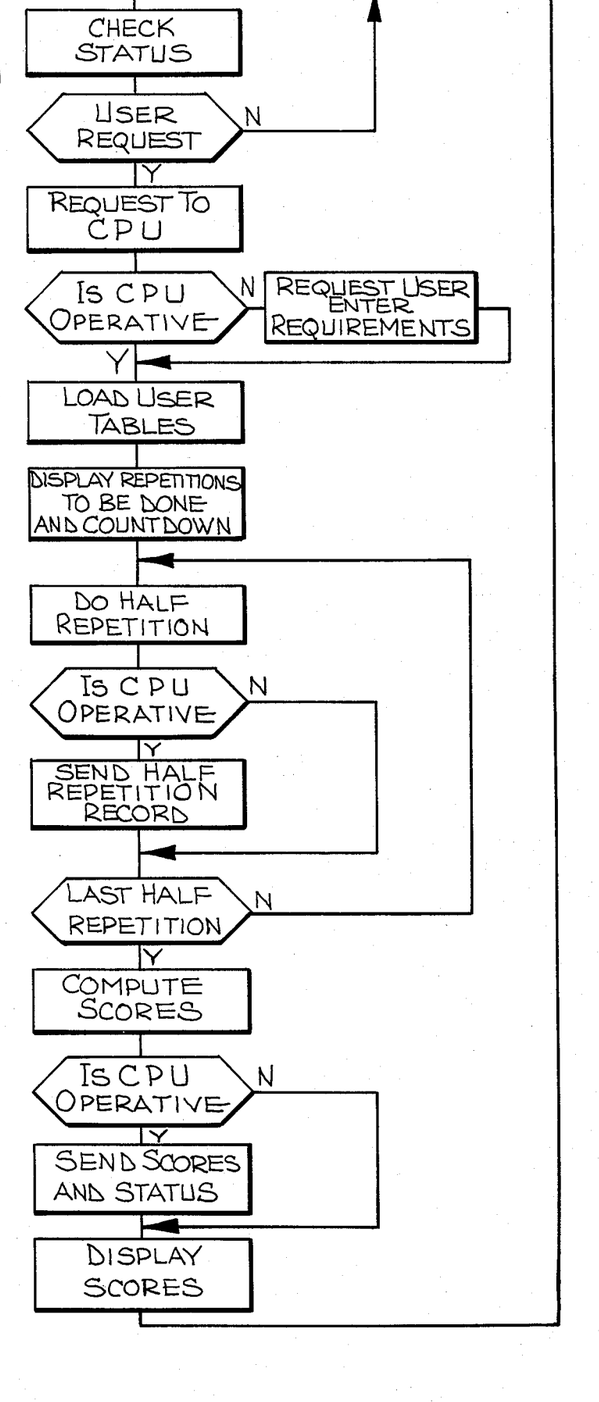
FIG. 7 is a simplified flow chart representing certain steps in the methods of this invention.

A simplified flow chart of the cooperation between a CPU and an MPU is represented in FIG. 7. As will be noted, information is transferred between the MPU and CPU upon completion of each body portion movement in one particular direction. That is, a "repetition" is considered to be a full cycle of force exertion. A "half repetition" represents one-half of a cycle of force exertion, during which one body portion is doing positive work and the other body portion is doing negative work, in the instance of the leg extension apparatus 20.

Figures 8, 9, 10, 11, 12:
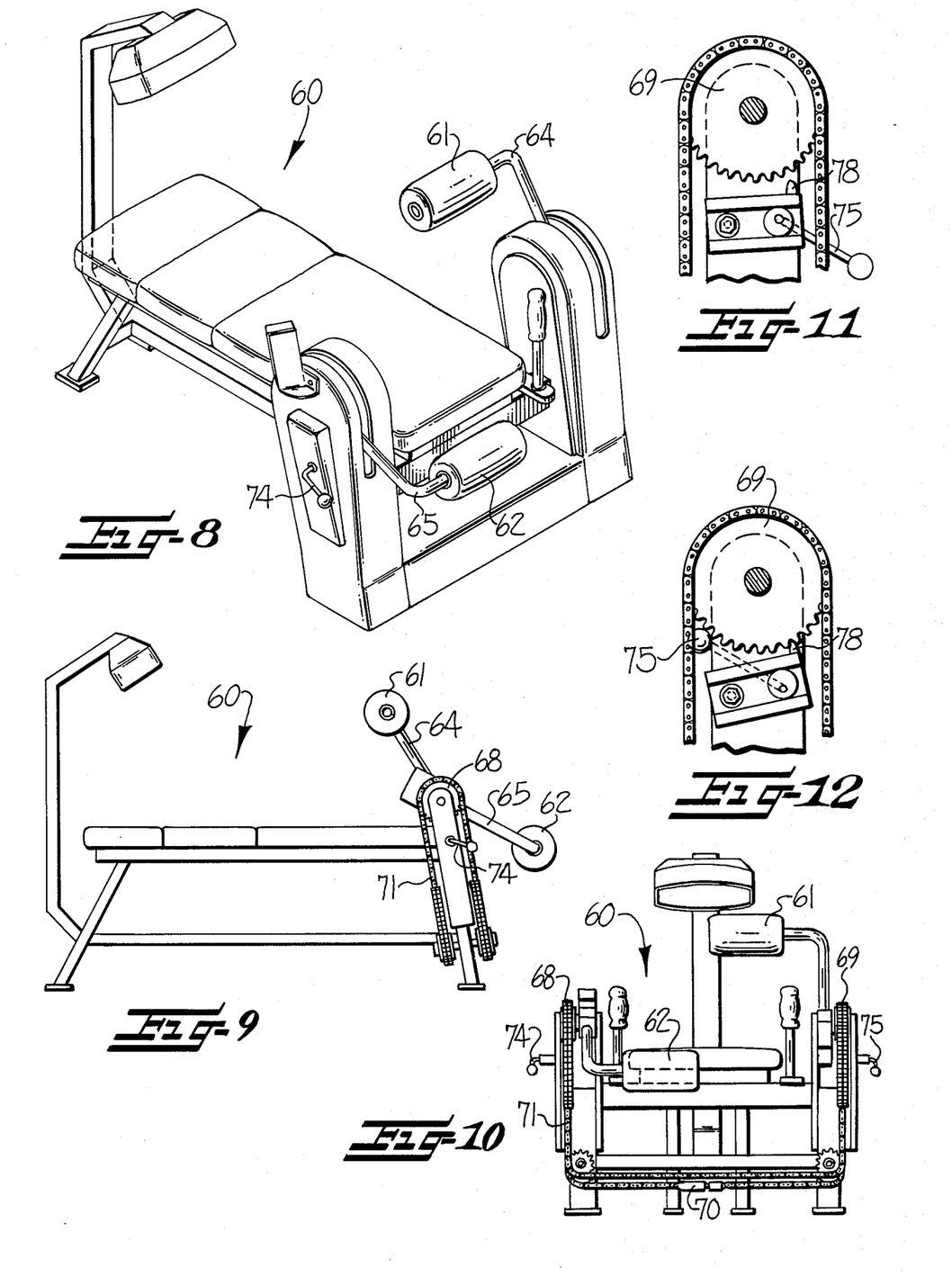
FIG. 8 is a view similar to FIG. 1 of a second type of exercise apparatus in accordance with the present invention.
FIG. 9 is a view similar to FIG. 2 of the exercise apparatus of FIG. 8.
FIG. 10 is a view similar to FIG. 3 of the exercise apparatus of FIG. 9.
FIGS. 11 and 12 are enlarged elevation views showing certain details of the apparatus of FIGS. 8 through 10.

As mentioned briefly above, it is contemplated that the present invention has utility with a number of exercise apparatus other than the leg extension apparatus 20 described hereinabove. For purpose of illustrating a different type of apparatus, FIGS. 8 through 12 have been included as showing a type of apparatus known as a hip-back apparatus. In using the hip and back apparatus generally indicated at 60, an exercising person assumes a supine position with the hip joints aligned with the axis of rotation of a pair of roll members 61, 62. The hip and back exercise apparatus 60 includes, as shown in FIGS. 8 through 10, a display generally indicated at 40 identical with the display used with the leg extension machine shown in FIGS. 1 through 3.

The hip and back apparatus 60 is constructed and operates in a manner generally comparable to the leg extension apparatus 20 of FIGS. 1 through 3 as described more fully hereinabove. The hip and back apparatus 60 includes a chain 71 trained about a pair of sprockets 68, 69 so that arms 64, 65 mounting the roll members 61, 62 move in opposite directions with coordinated movement. A load cell 70 is incorporated in the chain.

The hip and back apparatus 20 makes more clear the use of apparatus in accordance with the present invention as a force measuring apparatus or tensiometer. More particularly, first and second locking levers 74, 75 are provided and are actuable by a user of the machine to lock respective ones of the sprockets 68, 69 against rotation. As made more clear by FIGS. 11 and 12, such locking of a sprocket 69 against rotation occurs by insertion of a tooth or panel 78 into the teeth of the sprocket.

In using an apparatus in accordance with the present invention as a force measuring apparatus or tensiometer, a respective one of the arms 64, 65 is brought to a position in which a forced measurement is to be made and the sprocket at the opposite side of the machine is locked by operating the appropriate lever. Thus, if the force exerted by a left leg is to be measured by determining the force exerted against one roll member 61, the locking lever 74 on the opposite side of the apparatus 60 is actuated to lock the remote sprocket 68. Upon this occurrence, the load cell 70 is located in the "tight side" of the closed loop of the chain 71. Thus, force exerted by a user of the apparatus 60 would be developed statically, with the body portion through which force was being exerted blocked against movement in the direction that force was being exerted, and force measurements would be available from a range of positions.

As will be appreciated, use of exercise apparatus as described hereinabove with particular reference to two specific forms opens possibilities for accurate determination of effort expended during an exercise regimen. By the same token, goals for an exercise regimen may be established from a basis of knowledge concerning an individual's abilities to sustain an extended effort and a desired goal for such an ability. Finally, where an individual's starting ability and a desired goal can both be adequately represented from information monitored and prosessed by the apparatus as described above, then the exercise activity of a user may be directed by means of the display 40 so as to optimize achievement of the established goals.

In the drawings and specification, there has been set forth a preferred embodiment of the invention, and although specific terms are employed, they are used in a generic and descriptive sense only and not for purposes of limitation.

That which is claimed is:

1. Exercise apparatus for providing a user with a range of exercise movements and recording a measure of the effort exerted, said apparatus including:

first body engaging means adapted to be contacted by a first portion of a user's body and to be moved therewith;

second body engaging means adapted to be contacted by a second portion of a user's body and to be moved therewith;

interconnecting means linking said first and second body engaging means in a force transmitting passive relationship for effecting predetermined coordinated movement of said first and second body engaging means with respect to one another, said interconnecting means converting positive musculature work applied to one of said body engaging means to negative musculature work supplied to said other body engaging means, there being substantially no other forces applied to and no resistive forces acting upon said body engaging means, whereby all forces and resistances are provided solely by the user and may be instantaneously varied by said user;

force sensing means operatively connected to said interconnecting means and producing an output signal proportional to the magnitude of the force applied to at least one of said body engaging means;

position sensing means operatively connected to said interconnecting means and producing an output signal proportional to the position of at least one of said body engaging means;

processing means responsive to said force sensing means and said position sensing means to provide an output signal proportional to the physical effort exerted by the user as represented by the applied forces and changes of position; and display means responsive to said processing means output signal to generate a cognizable display.

2. Exercise apparatus for providing a user with a range of exercise movements and recording a measure of the effort exerted, said apparatus including:

first body engaging means adapted to be contacted by a first portion of a user's body and to be moved therewith;

second body engaging means adapted to be contacted by a second portion of a user's body and to be moved therewith;

interconnecting means linking said first and second body engaging means in a force transmitting passive relationship for effecting predetermined coordinated movement of said first and second body engaging means with respect to one another, said interconnecting means converting positive musculature work applied to one of said body engaging means to negative musculature work supplied to said other body engaging means, there being substantially no other forces applied to and no resistive forces acting upon said body engaging means, whereby all forces and resistances are provided solely by the user and may be instantaneously varied by said user;

force sensing means operatively connected to said interconnecting means and producing an output signal proportional to the magnitude of the force applied to at least one of said body engaging means;

position sensing means operatively connected to said interconnecting means and producing an output signal proportional to the position of at least one of said body engaging means;

processing means responsive to said force sensing means and said position sensing means to provide an output signal proportional to the physical effort exerted by the user as represented by the applied forces and changes of position;

selectively programmable standard producing means to provide an output signal proportional to the desired amount of physical effort to be exerted by an exercising person; and display means responsive to said processing means output signal and said standard producing output signal to generate a cognizable display.

3. The exercise apparatus of claim 1 or 2 wherein said interconnecting means includes rotational means connected to said first and second body engaging means, said rotational means having an axis of rotation coaxial with an axis of rotation of said contacted portion of said user's body to constrain movement of said first and second body engaging means to an arcuate movement corresponding to the natural arcuate movement of said contacted portion of said user's body.

4. The exercise apparatus of claim 3 wherein said rotational means is coaxial with a user's body joint.

5. The exercise apparatus of claim 1 or 2 wherein said interconnecting means includes non-extensible means connecting said first and second body engaging means.

6. The exercise apparatus of claim 1 or 2 wherein said interconnecting means includes a first rotational means operatively connected to said first body engaging means for rotation therewith; a second rotational means operatively connected to said second body engaging means for rotation therewith; and connecting means operatively connecting said first and second rotational means so that rotation of one rotational means results in rotation of said other rotational means.

7. The exercise apparatus of claim 1 or 2 wherein movement of said first body engaging means in one direction results in movement of said second body engaging means in an opposite direction.

8. The apparatus of claim 1 or 2 wherein said force sensing means includes an electromechanical strain gauge that provides an electrical output signal.

9. The apparatus of claim 1 or 2 wherein said position sensing means produces an electrical output signal.

10. The apparatus of claim 1 or 2 wherein said processing means includes a programmed microprocessor.

11. The apparatus of claim 1 or 2 wherein said display means comprises a plurality of light emitting diodes in a predetermined array, each light emitting diode response to a predetermined signal from said processing means.

12. The apparatus of claim 1 or 2 wherein said display means comprises a cathode ray tube means.

13. Exercise apparatus for providing a user with a range of exercise movements for muscles effecting movement at a selected body joint and for recording a measure of the effort exerted, said apparatus including:

first body engaging means adapted to contact a first portion of the user's body and move therewith along an arcuate path;

second body engaging means adapted to contact a second portion of a user's body and move therewith along an arcuate path;

first rotational means disposed coaxial to a first body joint, said first body engaging means connected thereto at a predetermined radial distance therefrom;

second rotational means disposed coaxial to a second body joint, said second body engaging means connected thereto at a predetermined radial distance therefrom;

interconnecting means linking said first and second rotational means in a force transmitting passive relationship for effecting predetermined coordinated reciprocal movement of said first and second body engaging means with respect to one another, said interconnecting means comprising a bidirectional force transmitting means that converts positive musculature work applied to one of said body engaging means to negative musculature work supplied to said other body engaging means, there being substantially no other forces or resistances applied to said body engaging means;

force sensing means operatively connected to said interconnecting means and producing an electrical output signal proportional to the magnitude of the force applied to at least one of said body engaging means;

position sensing means operatively connected to at least one of said rotational means and producing an electrical output signal proportional to the position of at least one of said body engaging means;

processing means responsive to said force sensing means and said position sensing means to provide one or more electrical output signals proportional to the physical effort exerted by the user as represented by the applied forces and changes of position; and display means responsive to said processing means output signal to generate a cognizable display.

14. The exercise apparatus of claim 13 wherein each of said rotational means comprises a chain sprocket.

15. The exercise apparatus of claim 13 wherein said bilateral force transmitting means comprises a closed loop chain.

16. The exercise apparatus of claim 1, 2 or 13 wherein one of said body engaging means includes a selectively-engageable locking pawl to prevent movement of both of said body engaging means.

17. A method of providing a user with a range of exercise movements and recording a measure of the physical effort exerted by said user, said exercise being conducted on apparatus having first and second body engaging means interconnected in a passive, force transmitting relationship, said method comprising
- moving the first body engaging means by applying a positive muscular force thereto;
- simultaneously moving the second body engaging means by applying a negative muscular force thereto;
- transmitting the muscular force applied to said first body engaging means to said second body engaging means and vice versa to impose resistance to each body engaging means in opposition to the respective muscular force applied thereto by said user, there being substantially no other forces or resistances applied thereto;
- sensing the amount of force applied to at least one of said body engaging means and producing a signal proportional thereto;
- sensing the amount of movement of at least one of said body engaging means and producing a signal proportional thereto;
- processing said force signals and said movement signals to provide an output signal proportional to the physical effort exerted by said user as represented by said force signals and movement signals; and
- displaying a cognizable image representing the amount of physical effort exerted, said image being generated in response to the output signal resulting from the processing of said force signals and said output signals.

18. A method of providing a user with a range of exercise movements and recording a measure of the physical effort exerted by said user, said exercise being conducted on apparatus having first and second body engaging means interconnected in a passive, force transmitting relationship, said method comprising
- moving the first body engaging means by applying a positive muscular force thereto;
- simultaneously moving the second body engaging means by applying a negative muscular force thereto;
- transmitting the muscular force applied to said first body engaging means to said second body engaging means and vice verse to impose resistance to each body engaging means in opposition to the respective muscular force applied thereto by said user, there being substantially no other forces or resistances applied thereto;
- sensing the amount of force applied to at least one of said body engaging means and producing a signal proportional thereto;
- sensing the amount of movement of at least one of said body engaging means and producing a signal proportional thereto;
- processing said force signals and said movement signals to provide an output signal proportional to the physical effort exerted by said user as represented by said force signals and movement signals;
- providing a pacing signal from a selectively programmable source for perception by said user, said pacing signal proportional to the desired amount of physical effort to be exerted by said user; and
- displaying a cognizable image representing the pacing signal and the amount of physical work exerted, said image of the work exerted being generated in response to the output signal resulting from the processing of said force signals and said output signals.

* * * * *